United States Patent [19]

Ko et al.

[11] Patent Number: 5,767,069
[45] Date of Patent: Jun. 16, 1998

[54] CYCLOSPORINS

[75] Inventors: Soo Young Ko, London, Great Britain; Hans Kobel, Basel, Switzerland; Brigitte Besemér-Rosenwirth, Mödling, Austria; Dieter Seebach, Zürich, Switzerland; René P. Traber, Basel, Switzerland; Roland Wenger, Riehen, Switzerland; Pietro Bollinger, Bottmingen, Switzerland

[73] Assignee: Novartis AG, Basel, Switzerland

[21] Appl. No.: 427,312

[22] Filed: Apr. 24, 1995

Related U.S. Application Data

[63] Continuation of Ser. No. 232,795, Apr. 25, 1994, abandoned, which is a continuation of Ser. No. 57,067, May 3, 1993, abandoned, which is a continuation of Ser. No. 785,959, Oct. 31, 1991, abandoned.

[30] Foreign Application Priority Data

| Nov. 2, 1990 | [GB] | United Kingdom | 9023859 |
| Nov. 5, 1990 | [GB] | United Kingdom | 9023970 |
| Nov. 5, 1990 | [GB] | United Kingdom | 9023971 |
| Nov. 5, 1990 | [GB] | United Kingdom | 9023972 |
| Aug. 5, 1991 | [GB] | United Kingdom | 9116836 |

[51] Int. Cl.$^6$ .................. A61K 38/13; C07K 7/64
[52] U.S. Cl. .................. 514/11; 514/9; 514/2; 530/317; 930/270
[58] Field of Search .......... 514/9, 11, 2; 530/317; 930/270

[56] References Cited

U.S. PATENT DOCUMENTS

| 4,639,434 | 1/1987 | Wenger et al. | 514/317 |
| 4,771,122 | 9/1988 | Seebach | 530/317 |
| 4,798,823 | 1/1989 | Witzel | 514/11 |
| 4,814,323 | 3/1989 | Andrieu et al. | 514/11 |
| 5,122,511 | 6/1992 | Patchett et al. | 514/317 |

FOREIGN PATENT DOCUMENTS

| 283801 | 9/1988 | European Pat. Off. |
| 0373260 | 6/1990 | European Pat. Off. |
| 0300785 | 12/1993 | European Pat. Off. |
| 2155936 | 10/1985 | United Kingdom |

OTHER PUBLICATIONS

Durette et al., Transplantation Proceedings, vol. 44, No. 2, Seyyl. 2 (Apr., 1988) pp. 51–57.

Wenger, Sandorama, (1984), pp. 5–11.

Rosenwirth, et al., Antimicrobial Agents and Chemotherapy 1994, vol. 38, No. 8 pp. 1763–1772.

Billich, et al., Journal of Virology, Apr. 1995, pp. 2451–2461—vol. 69, No. 4.

Steinkasserer, et al., Journal of Virology, Feb. 1995, pp. 814–824—vol. 69, No. 2.

Thali, et al., Letters to Nature—vol. 372—24 Nov. 1994.

*Primary Examiner*—Ponnathapura Achutamurthy
*Assistant Examiner*—T. D. Wessendorf
*Attorney, Agent, or Firm*—Marla J. Mathias; Thomas O. McGovern

[57] ABSTRACT

Nonimmunosuppressant cyclosporin derivatives having cyclophilin-binding activity, for example, the compound, [MeIle]$^4$-ciclosporin, are useful in inhibiting HIV-1 replication in treating AIDS and AIDS related disorders.

6 Claims, 3 Drawing Sheets

CYCLOSPORINS

This is a continuation of application Ser. No. 08/232,795, filed Apr. 25, 1994, which in turn is a continuation of application Ser. No. 08/057,067, filed May 3, 1993, which in turn is a continuation of application Ser. No. 07/785,959, filed Oct. 31, 1991, all of which are now abandoned.

The present invention relates to novel cyclosporins, their use as pharmaceuticals and pharmaceutical compositions comprising them, as well as to processes for their production.

The cyclosporins comprise a class of structurally distinctive, cyclic, poly-N-methylated undecapeptides, commonly possessing pharmacological, in particular immunosuppressive, anti-inflammatory and/or antiparasitic activity. The first of the cyclosporins to be isolated was the naturally occurring fungal metabolite Ciclosporin or Cyclosporine, also known as cyclosporin A and commercially available under the Registered Trademark SANDIMMUN® or SANDIMMUNE®. Ciclosporin is the cyclosporin of formula A.

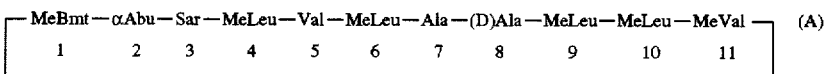

where MeBmt represents the N-methyl-(4R)-4-but-2E-en-1-yl-4-methyl-(L)threonyl residue of formula B

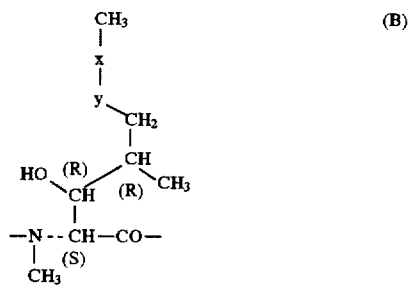

in which -x-y- is —CH=CH— (trans).

Figure 1:
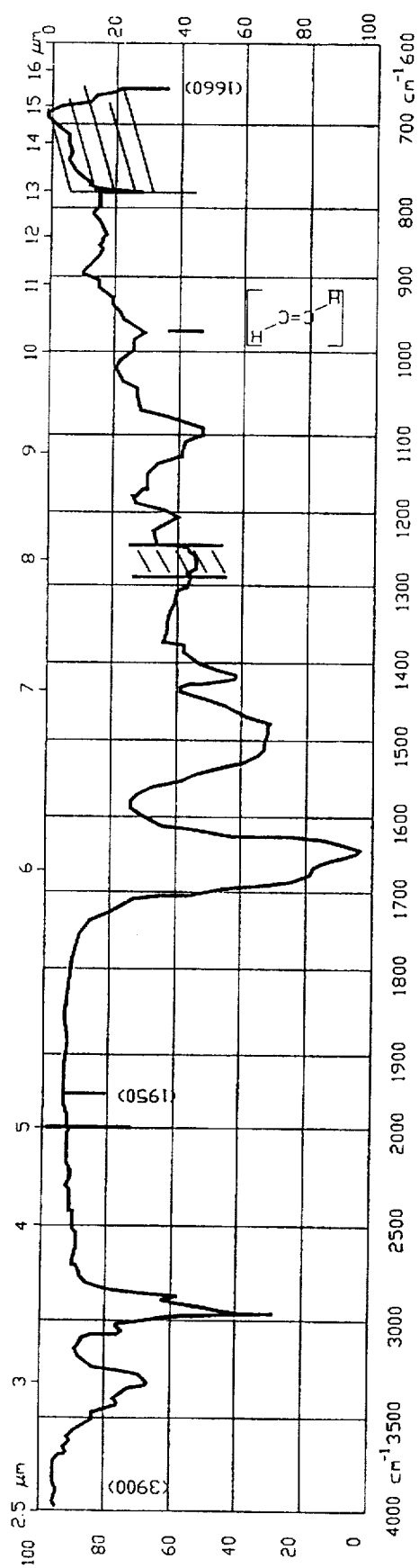
FIG. 1 is the IR spectrum in $CH_2Cl_2$ of ciclosporin.

Since the original discovery of Ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [cf. Traber et al; 1, Helv. Chim. Acta, 60, 1247–1255 (1977); Traber et al; 2, Helv. Chim. Acta, 65, 1655–1667 (1982); Kobel et al, Europ. J. Applied Microbiology and Biotechnology, 14, 273–240 1982); and von Wartburg et al, Progress in Allergy, 38, 28–45, 1986)], as well as various non-natural cyclosporin derivatives and artificial or synthetic cyclosporins including dihydro-cyclosporins [in which the moiety -x-y- of the MeBmt residue (formula B above) is saturated to give -x-y-=—$CH_2$—$CH_2$—]; derivatised cyclosporins (e.g. in which the 3'—O-atom of the MeBmt residue is acylated or a further substituent is introduced at the α-carbon atom of the sarcosyl residue at the 3-position); cyclosporins in which the MeBmt residue is present in isomeric form (e.g. in which the configuration across positions 6' and 7' of the MeBmt residue is cis rather than trans); and cyclosporins in which variant amino acids are incorporated at specific positions within the peptide sequence, e.g. employing the total synthetic method for the production of cyclosporins developed by R. Wenger—see e.g. Traber et al. 1, Traber et al, 2 and Kobel et al., loc. cit.; U.S. Pat. Nos. 4,108,985, 4,220,641, 4,288,431, 4,554,351, 4,396,542 and 4,798,823 European Patent Publications Nos. 34,567A, 56,782A, 300,784A, 300, 785A and 414,632A; International Patent Publication No WO 86/02080 and UK Patent Publications Nos. 2,206,119 and 2,207,678; Wenger 1, Transpl. Proc., 15 Suppl. 1:2230 (1983); Wenger 2., Angew. Chem. Int. Ed. 24 77 (1985) and Wenger 3., Progress in the Chemistry of Organic Natural Products, 50, 123 (1986).

The class comprised by the cyclosporins is thus now very large indeed and includes, for example, $[Thr]^2$-, $[Val]^2$-, $[Nva]^2$- and $[Nva]^2$-$[Nva]^5$-Ciclosporin (also known as cyclosporins C, D, G and M respectively), [3-O-acetyl-MeBmt]$^1$-Ciclosporin (also known as cyclosporin A acetate), [Dihydro-MeBmt]$^1$-[Val]2-Ciclosporin (also known as dihydro-cyclosporin D), [(D)Ser]$^8$-Ciclosporin, [MeIle]$^{11}$-Ciclosporin, [(D)MeVal]$^{11}$-Ciclosporin (also known as cyclosporin H), [MeAla]$^6$-Ciclosporin, [(D)Pro]$^3$-Ciclosporin and so on.

In accordance with conventional nomenclature for cyclosporins, these are defined throughout the present specification and claims by reference to the structure of Ciclosporin (i.e. Cyclosporin A). This is done by first indicating those residues in the molecule which differ from those present in Ciclosporin and then applying the term "Ciclosporin" to characterise the remaining residues which are identical to those present in Ciclosporin. At the same time the prefix "dihydro" is employed to designate cyclosporins wherein the MeBmt residue is hydrogenated (dihydro-MeBmt) i.e. where -x-y- in formula B is —$CH_2$—$CH_2$—. Thus [Thr]$^2$-Ciclosporine is the cyclosporin having the sequence shown in Formula A but in which αAbu at the 2-position is replaced by Thr, and [Dihydro-MeBmt]$^1$-[Val]$^2$-Ciclosporin is the cyclosporin having the sequence shown in Formula A but in which the MeBmt residue at position 1 is hydrogenated and αAbu at the 2-position is replaced by Val.

In addition, amino acid residues referred to by abbreviation, e.g. Ala, MeVal, αAbu etc. are, in accordance with conventional practice, to be understood as having the (L)-configuration unless otherwise indicated, e.g. as in the case of "(D)Ala". Residue abbreviations preceded by "Me" as in the case of "MeLeu", represent α-N-methylated residues. Individual residues of the cyclosporin molecule are numbered, as in the art, clockwise and starting with the residue MeBmt or dihydro-MeBmt in position 1. The same numerical sequence is employed throughout the present specification and claims.

It is now well established that Ciclosporin acts by interfering with the process of T cell activation by blocking transcription initiation of IL-2, although the precise mechanism has not yet been elucidated. Ciclosporin has been shown to form a complex with a 17 kD cytosolic protein (cyclophilin) that occurs in many cell types and has been shown to be identical to peptidyl-prolyl cis-trans isomerase, an enzyme involved in protein folding. Up to now, however, it has not been clear whether binding to cyclophilin is directly correlated with immunosuppressive activity in cyclosporins, or indeed whether cyclophilin binding is itself a sufficient criterion for immunosuppressive activity.

It has now been found that there are cyclosporins which bind strongly to cyclophilin, but are not at all immunosuppressive. It therefore follows that binding to cyclophilin is a necessary, but not a sufficient, criterion for immunosuppressant activity.

The present invention provides cyclosporins which are active against HIV-1 replication.

Human immune deficiency virus (HIV) infects preferentially T-helper (T4) lymphocytes, although it replicates also in various other cell types, especially those of the monocytic lineage. It causes a slowly progressing disease of the immune system characterised by a gradual T4-cell destruction, named AIDS. Other immunological abnormalities of AIDS are increase of cytotoxic/suppressor (T8) lymphocytes, a defect in the antigen presentation/recognition process and polyclonal activation of B-cells. The mechanism of T4-cell destruction is still not clear. Relatively few T4-cells seem to be infected, thus, a direct cytopathic effect caused by the virus may not be the only reason for T4-cell depletion. It has been hypothesised that T4-cell destruction could be amplified by an autoimmune process triggered by HIV-producing or HIV-protein-coated T4-cells. This continuous antigenic stimulation may lead to a state of permanent activation of T4-cells which would enhance HIV-replication in these cells and expand T-cytotoxic clones. Uninfected T4-cells may be rendered antigenic by binding exogenous viral gp120 to their CD4 molecules and would thus be a target of a T-cytotoxic response.

U.S. Pat. No. 4,814,323 discloses that Ciclosporin has activity against AIDS, and that in general "cyclosporins known as immunosuppressors" may be useful in this indication. There is no suggestion that non-immunosuppressive cyclosporins might be expected to have this property.

Surprisingly, it has now been found that cyclosporins which bind to cyclophilin, but are not immunosuppressive, exhibit an inhibitory effect upon HIV-1 replication.

A cyclosporin is considered as binding to cyclophilin if it binds to human recombinant cyclophilin at least one fifth as well as does Ciclosporin in the competitive ELISA test described by Quesniaux in Eur. J. Immunol. 1987 17 1359-1365. In this test, the cyclosporin to be tested is added during the incubation of cyclophilin with coated BSA-Ciclosporin and the concentration required to give a 50% inhibition of the control reaction without competitor is calculated ($IC_{50}$). The results are expressed as the Binding Ratio (BR), which is the log to the base 10 of the ratio of the $IC_{50}$ of the test compound and the $IC_{50}$ in a simultaneous test of Ciclosporin itself. Thus a BR of 1.0 indicates that the test compound binds cyclophilin one factor of ten less well than does Ciclosporin, and a negative value indicates binding stronger than that of Ciclosporin.

The cyclosporins active against HIV have a BR lower than 0.7, (since $\log_{10} 5 = 0.7$ approx), preferably equal to or lower than zero.

A cyclosporin is considered to be non-immunosuppressive when it has an activity in the Mixed Lymphocyte Reaction (MLR) of no more than 5%, preferably no more than 2%, that of Ciclosporin. The Mixed Lymphocyte Reaction is described by T.Meo in "Immunological Methods", L. Lefkovits and B. Peris, Eds., Academic Press, N.Y. pp. 227–239 (1979). Spleen cells ($0.5 \times 10^6$) from Balb/c mice (female, 8–10 weeks) are co-incubated for 5 days with $0.5 \times 10^6$ irradiated (2000 rads) or mitomycin C treated spleen cells from CBA mice (female, 8–10 weeks). The irradiated allogeneic cells induce a proliferative response in the Balb c spleen cells which can be measured by labeled precursor incorporation into the DNA. Since the stimulator cells are irradiated (or mitomycin C treated) they do not respond to the Balb/c cells with proliferation but do retain their antigenicity. The $IC_{50}$ found for the test compound in the MLR is compared with that found for Ciclosporin in a parallel experiment.

The activity of cyclosporins as inhibitors of HIV-1 replication may be demonstrated in the following test systems:

1. Inhibition of HIV-1-induced cytopathic effect in MT4-cells

The assay procedure described by Pauwels et al., J. Virol. Meth. 20/309 (1988), is used with minor modifications. The HTLV-I-transformed T4-cell line, MT4, which was previously shown to be highly permissive for HIV-infection, is used as the target cell. Inhibition of HIV-1, strain HTLV-IIIB-induced cytopathic effect is determined by measuring the viability of both HIV-infected and mock-infected cells. Viability is assessed spectrophotometrically via in situ reduction of 3-(4,5-di-methylthiazol-2-yl)-2,5-diphenyltetrazoliumbromide (MTT). Virus-infected and uninfected cultures without compound are included as controls as are uninfected cells treated with compound. The cell concentration is chosen so that the number of cells per ml increases by a factor of 10 during the 4 days of incubation in the mock-infected cultures. Virus inoculum is adjusted so as to cause cell death in 90% of the target cells after 4 days of incubation. The virus is adsorbed onto a 10-fold concentrated cell suspension at 37° C. for 1 hour. Then, the infected cells are diluted 1:10 and added to microtiter plates containing the test compound.

2. Cytotoxicity

To evaluate the anti-HIV potential in additional cell lines and particularly in a monocytic cell line (U937), cellular toxicity of the test compound to these cell lines is first assessed. Jurkat and U937 cell suspensions are adjusted to $1 \times 10^5$ cells/ml and incubated in the presence of various concentrations of test compound. After 48 hours the amounts of cells per ml are compared by staining with MTT. Cytoxicity in MT4 cells may be measured in the same way.

3. Inhibition of HIV-1 replication in Jurkat and U937 cells

The T4-cell line Jurkat and the monocytic cell line U937 are infected by suspending the cells 10-fold concentrated in virus solution. Adsorption is allowed for 2 hours at 37° C. The cells are then spun down, the inoculum is removed and the cells are resuspended at their original concentration in fresh culture medium containing test compound. Thus, the substance is added post adsorption. At days 2, 5, 8, 12, 15 and 19 post-infection, aliquots of the infected cultures are removed. Cells are spun down and the supernatants collected. The concentration of viral p24 antigen is determined in the supernatants by means of a commercial ELISA kit and serves as a parameter for virus production. After each removal of aliquots, cells are counted and adjusted to $2 \times 10^5$ cells/ml by adding fresh medium containing the test compound at the particular concentration.

Of the compounds according to the invention, i.e. non-immunosuppressive, cyclophilin-binding cyclosporins active against HIV-1 (Active Compounds), some are novel and others are known; however the anti-HIV activity of the known Active Compounds has not previously been disclosed, and in many cases the known Active Compounds have not been disclosed to have any pharmaceutical activity whatsoever.

It is found that many of the Active Compounds have structures differing from that of Ciclosporin specifically at the 4 and/or 5 positions.

One group of Active Compounds are cyclosporins in which the MeLeu group at position 4 is replaced by a different N-methylated amino acid, for example γ-hydroxy-MeLeu, MeIle, MeVal, MeThr or MeAla. In addition to MeIle and MeThr, the allo-forms MeaIle and MeaThr may also be used. In the allo-form, the stereochemistry at the β-position has the opposite configuration to that of the natural amino acid, so that the normal form and the allo-form constitute a pair of diastereoisomers.

A further group of Active Compounds is that in which Val at the 5-position is replaced by an N-alkyl-, preferably N-methyl-, amino acid. Preferably the amino acid which is N-alkylated is Val or Leu. Preferably the hydrogen of the imino group of [Val]$^5$ is replaced by a non-branched $C_{1-6}$alkyl group, preferably methyl, ethyl or n-propyl, particularly methyl. The latter preferred group of Active Compounds are all novel.

Additionally or alternatively, certain Active Compounds may differ from Ciclosporin at the 1, 2, 3, and/or 6 positions. A preferred group of Active Compounds is constituted by the compounds of Formula I:

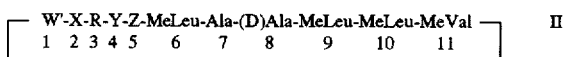

in which

W is MeBmt, dihydro-MeBmt or 8'-hydroxy-MeBmt;

X is αAbu, Val, Thr, Nva or 0-methyl threonine (MeOThr);

R is Sar or (D)-MeAla;

Y is MeLeu, γ-hydroxy-MeLeu, MeIle, MeVal, MeThr, MeAla, MeaIle or MeaThr;

Z is Val, Leu, MeVal or MeLeu; and

Q is MeLeu, γ-hydroxy-MeLeu or MeAla;

provided that when Y is MeLeu then either Z is MeVal or MeLeu, or W is 8'-hydroxy-MeBmt.

The groups W,X,Y,Z,Q and R have, independently, the following preferred significances:

W is preferably W' where W' is MeBmt or dihydro-MeBmt;

X is preferably X' where X' is αAbu or Nva, more preferably X" where X" is αAbu;

R is preferably R' where R' is Sar;

Y is preferably Y' where Y' is γ-hydroxy-MeLeu, MeVal, MeThr or MeIle;

Z is preferably Z' where Z' is Val or MeVal; and

Q is preferably Q' where Q' is MeLeu;

One especially preferred group of Active Compounds are the compounds of Formula I in which W is W', X is X', Y is Y', Z is Z', Q is Q' and R is R'.

Particularly preferred compounds of Formula I are:

a) [dihydro-MeBmt]$^1$-[γ-hydroxy-MeLeu]$^4$-Ciclosporin b) [MeVal]$^4$-Ciclosporin c) [MeIle]$^4$-Ciclosporin d) [MeThr]$^4$-Ciclosporin e) [γ-hydroxy-MeLeu]$^4$-Ciclosporin f) [Nva]$^2$-[γ-hydroxy-MeLeu]$^4$-Ciclosporin g) [γ-hydroxy-MeLeu]$^4$-[γ-hydroxy-MeLeu]$^6$-Ciclosporin h) [MeVal]$^5$-Ciclosporin i) [MeOThr]$^2$-[(D)MeAla]$^3$-[MeVal]$^5$-Ciclosporin j) [8'-hydroxy-MeBmt]$^1$-Ciclosporin In addition, certain compounds not within the scope of Formula I are Active Compounds, for example k) [MeAla]$^6$-Ciclosporin, and l) [γ-hydroxy-MeLeu]$^9$-Ciclosporin.

The invention also provides novel Active Compounds, which are compounds of Formula II:

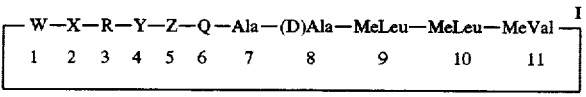

where W', X, R, Y and Z are as defined above, provided that 1) when Y is MeLeu or MeAla then Z is MeVal or MeLeu and 2) when W' is MeBmt, R is Sar, and Y is γ-hydroxy-MeLeu, then Z is other than Val.

A preferred group of novel Active Compounds consists of the compounds of Formula II in which X is X", Y is Y' and Z is Z', provided that when W' is MeBmt, Y' is other than γ-hydroxy-MeLeu.

Particularly preferred novel Active Compounds are the compounds a), b), c), d), f) and h) above. Certain of these compounds, for example compounds b) and c), are found to block the immunosuppressive action of Ciclosporin by blocking its binding to cyclophilin, and thus act as Ciclosporin antagonists.

The Active Compounds may be obtained in a variety of ways, which may be classified as:

1) Fermentation
2) Biotransformation
3) Derivatisation
4) Partial Synthesis
5) Total Synthesis.

1) Certain of the Active Compounds are produced as by-products of the fermentation of original or modified strains of Ciclosporin-producing organisms such as *Tolypocladium inflatum* Gams, as exemplified by the production of compound c), described in Example 1 below.

2) Other Active Compounds, including the known compounds j) and l) are metabolites of Ciclosporin, and can be isolated by chromatographic methods from the urine of humans or animals dosed with Ciclosporin. Furthermore, these and other metabolic transformations are possible using microorganisms, for example the production of compounds e) and g) by biotransformation of cyclosporin A, as described in Examples 2 and 3, or that of compound f) by biotransformation of cyclosporin G (Example 4). These examples demonstrate a novel process for the preparation of cyclosporins having one or more γ-hydroxy-MeLeu residues, comprising the steps of culturing a novel modified strain of *Sebekia benihana*, adding a cyclosporin having one or more MeLeu residues, and isolating the product from the fermentation broth.

3) By derivatisation is meant that natural or synthetic cyclosporins may be converted into Active Compounds by one or more chemical reactions in which one or more of the amino acids are modified without the peptide bonds being opened and reformed. For example, the class of Active Compounds in which the Val at position 5 is N-alkylated may be obtained by reacting the corresponding cyclosporin having Val at position 5 with butyllithium, followed by reaction with an alkylating agent, as exemplified for compound h) in Example 5 and for compound i) in Example 6.

As further examples, compound a) may be prepared by hydrogenation of compound e) (Example 7), and compound j), which is also a major metabolite of Ciclosporin, may be prepared from the known compound Ciclosporin acetate as described in Example 8.

4) The term partial synthesis is used to mean a series of chemical reactions in which the ring of a natural cyclosporin is opened, one or more amino acids are removed, different amino acids are added, and the ring is closed again.

5) The total synthesis of cyclosporins may be carried out by building up a linear undecapeptide and cyclising, as described by Wenger (loc. cit.), see also U.S. Pat. Nos. 4,396,542 and 4,798,823. In principle, any cyclosporin may be prepared by the total synthesis route, although where one of the other methods is available, this may well be more convenient than total synthesis. Total synthesis may be used for the preparation of compound d) (Example 9), and for the known metabolite compound 1).

Compound k) is a known substance whose properties have been described by Quesniaux et al (*Mol. Immunol.* 24 1159 1987) and which can also be prepared by total synthesis. For example, a total synthesis of this compound is described in U.S. Pat. No. 4,914,188.

EXAMPLE 1

[MeIle]$^4$ -Ciclosporin (Compound c)

Producing Strain

Compound c) is obtained by fermentation of the fungal strain *Tolypocladium inflatum* Cy E 4556, deposited at the Deutsche Sammlung für Mikroorganismen under the provisions of the Budapest treaty on 24 Jul. 1991 under the accession number DSM 6627. This strain is a mutant of the strain NRRL 8044 of the species *Tolypocladium inflatum* Gams, and is taxonomically identical with the parent strain, which has been fully described, e.g. in British Patent 1,491, 509.

Culture 1. Agar starting culture: Agar slant cultures of the strain DSM 6627 are grown for 14 days at 27° C. on the following agar medium:

| | |
|---|---|
| Yeast extract (Gistex) | 4 g |
| Malt extract (Wander) | 20 g |
| Agar | 20 g |
| Demineralised water to | 1000 ml. |

The medium has a pH of 5.4–5.6 and is sterilised for 20 min. at 120° C.

2. Preculture: Spores from the mycelium of 4 starting cultures are suspended in 40 ml of a 0.9% salt solution. A series of 500 ml Erlenmeyer flasks each containing 100 ml of preculture medium are inoculated each with 20 ml of this suspension. The composition of the preculture medium is as follows:

| | |
|---|---|
| Casein (Amber EHC) | 25 g |
| Maltose | 75 g |
| KH2PO4 | 1 g |
| KCl | 2.5 g |
| Demineralised water to | 1000 ml |

The medium is adjusted to pH 5.2–5.5 with HCl, then sterilised for 20 min. at 120° C. The precultures are fermented for 24 hr. at 27° C. on a rotary shaker at 200 rpm with an eccentricity of 50 mm.

3. Intermediate culture: One 25-liter steel fermenter containing 20 liters of preculture medium is inoculated with 200 ml of preculture. The intermediate culture is fermented during 5 days at 27° C., with a stirring rate of 150 rpm and a rate of air flow of 0.5 l/min. per liter medium at 0.5 bar pressure.

4. Main culture: 100 liter of preculture medium are inoculated with 10 l of intermediate culture and fermented in a 120-liter steel fermenter. To this medium is added 4 g/l D-Threonin, sterilised by filtration. Fermentation is carried out at 27° C. for 14 days, with a stirring rate of 70 rpm and a rate of air flow of 0.4 l/min per liter medium at 0.5 bar pressure being used for the 5 first days, the stirring rate then being increased to 100 rpm and the air flow rate to 0.5 l/min for the remainder of the fermentation period.

Isolation: The mycelium is separated from the culture medium and extracted in a Turrax apparatus by crushing and stirring 3 times with 10 liters of methanol/water (9:1 by vol.). The crushed mycelium is separated from the solvent by suction-filtration and the combined filtrates are concentrated by evaporation under vacuum at a temperature of 40° C. until the vapour consists mainly of water alone. The obtained mixture is extracted four times using 2 liters 1,2-dichloroethane at each extraction and the combined 1,2-dichloroethane solutions are concentrated by evaporation under vacuum at a temperature of $_{40}$° C.

The residue is subjected to silica gel column chromatography (10 kg of silica gel, granulate size 0.02–0.045 mm, "Grace") using ethyl acetate/water as eluent (fractions of 2.5 l). Fractions 20–23, containing [MeIle]$^4$-Ciclosporin are pooled and then further separated by silica gel column chromatography (600 g of silica gel, granulate size 0.04–0.063 mm, "Merck") using chloroform/methanol (98:2 by vol.) as eluent (fraction size 300 ml). Further purification is achieved by silica gel column chromatography (400 g of silica gel, granulate size 0.04–0.063 mm. "Merck") using methylene chloride/methanol (98:2 by vol.) as eluent (fraction size 200 ml) yielding pure [MeIle]$^4$-Ciclosporin as an amorphous white powder: m.p. 155°–158° C.; [α]20/D= −235° (c=0.68 in CHCl$_3$) and −193° (c=0.74 in CH$_3$OH).

Figure 2:
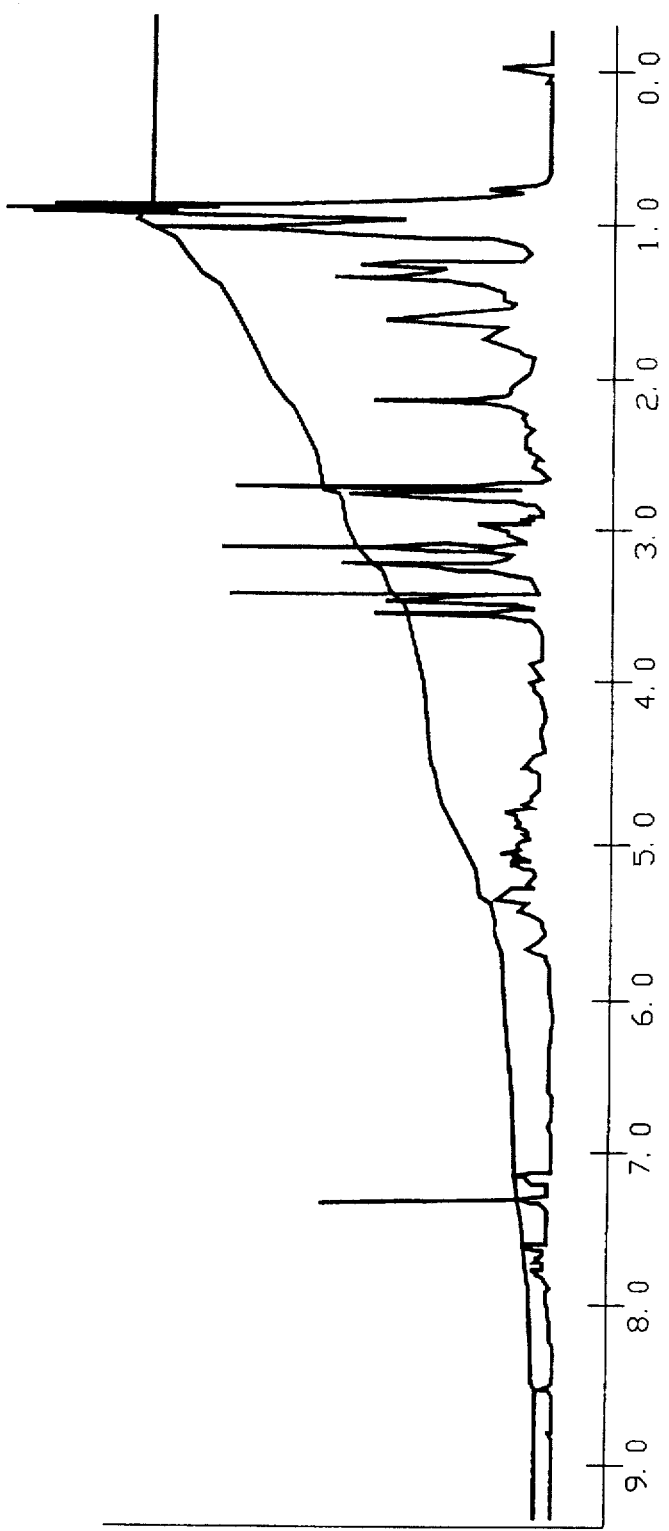
FIG. 2 is the proton NMR spectrum in $CDCl_3$ of ciclosporin.

The IR spectrum in CH$_2$Cl$_2$ is as shown in FIG. 1, and the proton NMR spectrum in CDCl$_3$ is as shown in FIG. 2.

EXAMPLE 2

[γ-hydroxy-MeLeu]$^4$-Ciclosporin (Compound e)

Compound e) is obtained from biotransformation of Ciclosporin by the microorganism *Sebekia benihana*. The original strain used is named NRLL 11111 and belongs to the species *Sebekia benihana* (Dietz and Li: Sebekia, a new genus of the family Actinoplanaceae. Abstrs. 82nd Ann.Meet.Amer.Soc.Microbiol., 163, Atlanta, 1982). This strain is able to hydroxylate novobiocin. The subcultured strain used for the preparation of compound e and related compounds has been deposited at the German Collection of Microrganisms (D-3300 Braunschweig) under the number DSM 6182.

1. Agar starting culture: Agar slant cultures of the strain DSM 6182 are grown for 10 days at 27° C. on the following agar medium:

| | |
|---|---|
| Glucose | 10 g |
| Starch (soluble) | 20 g |
| Yeast extract (Gistex) | 5 g |
| Peptone (N-Z-Amine Typ A, Sheffield) | 5 g |
| CaCO$_3$ | 1 g |

-continued

| Agar (Bacto) | 18 g |
| --- | --- |
| Demineralised water to up to 1 Liter. | | pH: neutralised at 7 with NaOH/$H_2SO_4$
Sterilisation: 120° C./20 min.

2. Preculture: Spores and mycelium of one starting culture are suspended in 10 ml of a 0.9% salt solution. A series of 200 ml Erlenmyer flasks each containing 50 ml of preculture medium are inoculated each with 5 ml of this suspension. The composition of the preculture medium is as follows:

| Glucose | 7 g |
| --- | --- |
| Starch (soluble) | 10 g |
| Yeast extract (Gistex) | 4.5 g |
| Malt extract (liquid, Wander) | 10 g |
| Peptone (N-Z-Amine Typ A, Sheffield) | 2.5 g |
| $CaCO_3$ | 1 g |
| Trace solution Nr 235 | 1 ml |
| Demineralised water to up to 1 Liter. | | pH neutralised to 7 with NaOH/$H_2SO_4$
Sterilisation: 120° C./20 min.
Trace solution Nr 235:

| $H_3BO_3$ | 0.1 g |
| --- | --- |
| $FeSO_4.7H_2O$ | 5 g |
| KI | 0.05 g |
| $CoCl_2.6H_2O$ | 2 g |
| $CuSO_4.5H_2O$ | 0.2 g |
| $MnCl_2.4H_2O$ | 2 g |
| $ZnSO_4.7H_2O$ | 4 g |
| Demineralised water up to 999 ml | |
| $H_2SO_4$ (97%) | 1 ml |

The precultures are fermented for 4 days at 27° C. on a rotary shaker at 200 rpm with an eccentricity of 50 mm.

3. Intermediate culture: A series of 200 ml Erlenmeyer flasks each containing 50 ml of the preculture medium are inoculated each with 5 ml of preculture. The intermediate culture is fermented for 3 days at 27° C. on a rotary shaker at 200 rpm with an eccentricity of 50 mmm.

4. Main culture: A series of 500 ml Erlenmeyer flasks each containing 50 ml of the main medium (total 12 liters) are inoculated each with 5 ml of intermediate culture. These cultures are fermented for 3 days at 27° C. on a rotary shaker at 200 rpm with an eccentricity of 50 mm. After 24 hours cyclosporin A (7.5 mg) solubilized in methanol is added to each main culture (=150mg/L).

The composition of the main culture medium is as follows:

| Cerelose | 10 g |
| --- | --- |
| Dextrine | 10 g |
| Starch (soluble) | 10 g |
| Yeast extract (Gistex) | 2.5 g |
| Soyabean flour (Nurupan, Edelsoya) | 12.5 g |
| $K_2HPO_4$ | 0.25 g |
| $KH_2PO_4$ | 0.12 g |
| $MgSO_4.7H_2O$ | 0.10 g |
| $CaCl_2.6H_2O$ | 0.05 g |
| Trace element solution AC-1 | 1 ml |
| Demineralised water up to 1 Liter. | | pH: adjusted at 7.2–7.5 (KOH/$H_2SO_4$)
Sterilisation: 120° C./ 20 min.

Trace element solution AC-1: This solution has the same composition as the solution Nr 235 with the addition of: $(NH_4)_6Mo_7O_{24}$ 0.2 g.

5. Isolation: The mycelium is separated from the culture medium and the resulting culture filtrate (13 L) is extracted three times with 1.2-dichloroethane using 1.5 L at each extraction. The combined 1.2-dichloroethane solutions are evaporated under vacuum at a temperature of 40° C. The crude residue is subjected to Sephadex LH-20 gel filtration using methanol as eluent. Those fractions containing the cyclosporin compounds (525 mg) are pooled and chromatographed on silica gel (50 g, granulate size 0.04–0.063 mm, 'Merck') using chloroform/methanol as eluent. Repeated chromatography using the same system yields pure [γ-hydroxy-MeLeu]$^4$-Ciclosporin as an amorphous white powder. m.p. 150°–153°, $[\alpha]_D^{20}$ −225° (c=0.53 in $CHCl_3$), −171° (c=0.44 in $CH_3OH$).

EXAMPLE 3

[γ-hydroxy-MeLeu]$^4$-[γ-hydroxy-MeLeu]$^6$-Ciclosporin (compound g)

The more polar side fractions originating from the purification of [γ-hydroxy-MeLeu]$^4$-Ciclosporin are further separated by repeated silica gel column chromatography (granulate size 0.04–0.063 mm) using acetone/hexane 2:1 as eluent followed by chromatography on silica gel using methyl t.butyl ether/methanol/water 90:9:1 as eluent. The first fractions contain [γ-hydroxy-Leu]$^4$-Ciclosporin which is further purified by decolorizing with charcoal yielding the pure compound as an amorphous white powder. m.p. 162°–164°, $[\alpha]_D^{20}$ −211° (c=0.50 in $CHCl_3$), −157° (c=0.52 in $CH_3OH$).

The later fractions from the above silica gel column chromatography contain [γ-hydroxy-MeLeu]$^4$-[γ-hydroxy-MeLeu]$^6$-Ciclosporin and are further purified by decolorizing with charcoal yielding the pure title compound as an amorphous white powder. m.p. 157°–160°, $[\alpha]_D^{20}$ −217° (c=0.54 in $CHCl_3$), −176° (c=0.42 in $CH_3OH$).

EXAMPLE 4

[Nva]$^2$-[γ-hydroxy-MeLeu]$^4$-Ciclosporin (compound f)

This compound is prepared by a procedure analogous to the preparation of compound e ([γ-hydroxy-MeLeu]$^4$-Ciclosporin), but using cyclosporin G ([Nva]2-Ciclosporin) as starting material. After purification by repeated silica gel column chromatography using ethyl acetate saturated with water and acetone/hexane 2:1 as eluent, respectively, the title compound is obtained as an amorphous white powder, m.p. 138°–141°, $[\alpha]_D^{20}$ −213° (c=0.69 in $CHCl_3$), −168° (c=0.70 in $CH_3OH$).

EXAMPLE 5

[MeVal]$^5$-ciclosporin (compound h)

Cyclosporin A (0.60 g=0.5 mmol) dissolved in tetrahydrofuran (20 ml) is incubated with 0.63 ml of a 1.6M solution of butyllithium (1.0 mmol) in hexane. The resulting solution is reacted with dimethyl sulphate (0.1 ml; 1.5 mmol) at −78° C. The reaction mixture is slowly warmed to room temperature and stirred overnight.

Figure 3:
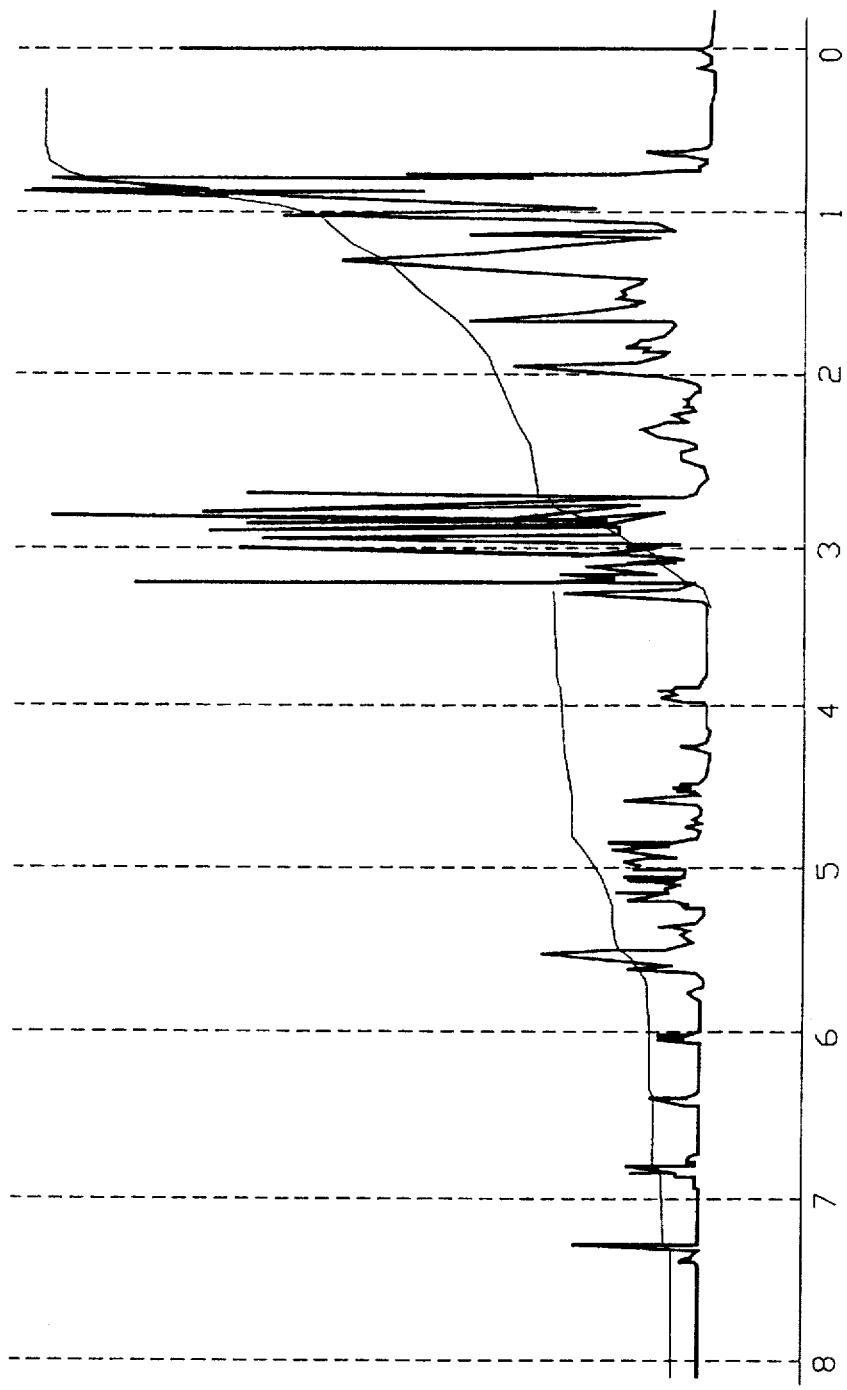
FIG. 3 is a 300 MHz HNMR spectrum in $CDCl_3$ of the product of Example 5.

Isolation by flash chromatography ($SiO_2$, 5% methanol/ether), followed by HPLC (reverse phase) gave the title product. The compound is characterised by a 300 MHz $^1$H NMR spectrum in $CDCl_3$ which is shown in FIG. 3.

EXAMPLE 6

[MeOThr]$^2$-[(D)MeAla]$^3$-[MeVal]$^5$-Ciclosporin (Compound i)

A mixture of 480 ml THF (absolute) and 6.96g (49.2 mMol) diisopropyl amine is cooled to −80° C., and 33.5 ml of a 1.33M solution of butyllithuim in hexane (=44.5 mMol) is added slowly through a syringe. The mixture is stirred for 30 min. at −80° C., then a solution of 8 g (6.6 mMol) cyclosporin C ([Thr]²-Ciclosporin) in 120 ml absolute THF is added through a syringe over 2–3 minutes. The clear solution is stirred for a further hour at −80° C., then 2.06 ml methyl iodide is slowly added.

The mixture is allowed to warm to room temperature over 2 hr, then 40 ml water is added and the solvents are evaporated on a rotary evaporator at 30° C./15 mm Hg. The residue is partitioned between water and ether, and the ether layer is washed four times with semi-saturated brine, dried over MgSO$_4$ and evaporated, to give a residue of 8.1 g.

The residue is chromatographed on 1200 g Kieselgel with water-saturated ethyl acetate, to give a crude product which after a further chromatography on 200 g Kieselgel with 5% MeOH/CH$_2$Cl$_2$ gives the pure title product, $[\alpha]_D^{20} = -195°$ (C=1.0 in CHCl$_3$).

EXAMPLE 7

[dihydro-MeBmt]-[γ-hydroxy-MeLeu]⁴-Ciclosporin (compound a)

To a suspension of 200 mg pre-hydrogenated 10% palladium/charcoal in 4 ml ethanol is added 1.2 g of [γ-hydroxy-MeLeu]⁴-Ciclosporin (compound e) in 10 ml ethanol and hydrogenation is carried out at room temperature until no more hydrogen is taken up. After removal of the catalyst by filtration the solution is evaporated, yielding the title compound as an amorphous white powder, m.p. 154°–156°, $[\alpha]_D^{20}$ −225° (c=0.87 in CHCl$_3$), −169° (c=0.70 in CH$_3$OH).

EXAMPLE 8

[8'-hydroxy-MeBmt]¹-Ciclosporin (compound j)

1. [O-acetyl-ω-bromo-MeBmt]¹-Ciclosporin: A mixture of 25.0 g (20 mmol) of [O-acetyl-MeBt]¹-Ciclosporin (Traber et al, Helv.Chim. Acta 1982, 65, 1653), 4.4 g (25 mmol) of N-bromo succinimide and 400 mg of azobisisobutyronitrile in 250 ml carbon tetrachloride is heated to reflux for 2.5 hrs. The solvent is evaporated and replaced by ether, filtered from solids, washed with water, dried over magnesium sulfate and evaporated to dryness. The residue is chromatographed over silica gel with ethyl ether/ethyl acetate (4:1) to give 10.7 g (40%) of amorphous product which is crystallized from ether/hexane to yield 8.4 g of pure substance; m.p. 207°–209° C. Later fractions of the chromatogram contained an additional 11.2 g of product of slightly lesser quality.

2. [O-acetyl-ω-acetoxy-MeBmt]¹-Ciclosporin: A mixture of 4.31 g (3.3 mmol) of the product of step 1 (contaminated with an estimated 15–20% of starting material) and 2.1 g (8 mmol) of tetraethylammonium acetate tetrahydrate in 30 ml of methyl ethyl ketone, containing a catalytic amount of sodium iodide, is heated in an oil bath at 105° C. for 3 hrs. and kept at room temperature over the weekend. The solvent is diluted with methyl t-butyl ether and washed with water and brine. The organic layer is dried over MgSO$_4$ and evaporated to leave 4.0 g of crude product which is purified on a RP-18 reverse phase column (240 g) to yield 3.07 g of the title product; m.p. 191°–192° C.

3. [ω-hydroxy-MeBmt]¹-Ciclosporin: A solution of 1.72 g (1.3 mmol) of the product of step 2 in 75 m of methanol and a solution of 1.2 g of sodium in 50 ml of methanol are mixed and kept at r.t. for 2.5 hours. Then the solution is acidified with acetic acid. The solvent is evaporated under reduced pressure and the residue is dissolved in methyl t-butyl ether, washed sequentially with water, brine, and sodium bicarbonate solution, dried over MgSO$_4$ and evaporated. The crude product (1.6 g) is eluted from a RP-18 column (240 g) with methanol/water 75:15 to give 1.5 g of pure product. A sample is crystallized from ether/hexane to give a crystalline product of m.p. 181°–183° C.

EXAMPLE 9

[MeThr]⁴-Ciclosporin (compound d)

The total synthesis of Ciclosporin as described in U.S. Pat. Nos. 4,396,542 and 4,798,823 is carried out using MeThr in the 4-position in place of MeLeu. The product has $[\alpha]_D^{20} = -249.6°$ (c=1.0 in CHCl$_3$).

EXAMPLE 10

[MeVal]⁴-Ciclosporin (compound b)

The total synthesis of Ciclosporin as described in U.S. Pat. Nos. 4,396,542 and 4,798,823 is carried out using MeVal in the 4-position in place of MeLeu. The product has $[\alpha]_D^{20} = -226°$ (c=0.358 in CHCl$_3$).

EXAMPLE 11

Immunosuppression and cyclophilin-binding of Active Compounds relative to Ciclosporin Table I gives examples of (1) the cyclophilin Binding Ratio (BR) of Active Compounds as measured in an ELISA assay and (2) the immunosuppressive activity of Active Compounds relative to Ciclosporin as measured in an MLR assay and expressed as a percentage of activity relative to Ciclosporin (Immunosuppressive Ratio or IR).

Further explanation of the significance of these values and the methods for conducting these tests are set forth supra.

TABLE I

| Compound | BR(log$_{10}$) | IR (%) |
|---|---|---|
| a) [dihydro-MeBmt]¹-[γ-hydroxy-MeLeu]⁴-Ciclosporin | 0.1 | <1 |
| b) [MeVal]⁴-Ciclosporin | 0.1 | <1 |
| c) [MeIle]⁴-Ciclosporin | −0.2 | <1 |
| e) [γ-hydroxy-MeLeu]⁴-Ciclosporin | −0.3 | <1 |
| f) [Nva]²-[γ-hydroxy-MeLeu]⁴-Ciclosporin | 0.4 | <1 |
| h) [MeVal]⁵-Ciclosporin | 0.4 | 5.3 |
| j) [8'-hydroxy-MeBmt]¹-Ciclosporin | 0.35 | 1.8 |
| k) [MeAla]⁶-Ciclosporin | −0.4 | 3.2 |
| l) [γ-hydroxy-MeLeu]⁹-Ciclosporin | 0.15 | 2.9 |

EXAMPLE 12

Anti-HIV activity and cytotoxicity of Active Compounds

Examples of the activity of Active Compounds and Ciclosporin as inhibitors of HIV-1 replication in MT4-cells and the cytotoxicity of Active Compounds and Ciclosporin in MT4-cells are set forth in Table II. The significance of these numbers and the appropriate methods are discussed supra.

TABLE II

| Compound | Cytotoxicity (μg/ml) | Anti-HIV (IC$_{50}$) |
|---|---|---|
| a) [dihydro-MeBmt]¹-[γ-hydroxy-MeLeu]⁴-Ciclosporin | 16.3 | 0.12 |
| b) [MeVal]⁴-Ciclosporin | 5.4 | 0.064 |
| c) [MeIle]⁴-Ciclosporin | 4.5 | 0.056 |
| e) [γ-hydroxy-MeLeu]⁴-Ciclosporin | 15.5 | 0.34 |
| f) [Nva]²-[γ-hydroxy-MeLeu]⁴-Ciclosporin | 14.0 | 0.85 |

TABLE II-continued

| Compound | Cytotoxicity (μg/ml) | Anti-HIV (IC$_{50}$) |
|---|---|---|
| h) [MeVal]$^5$-Ciclosporin | 4.4 | 0.45 |
| i) [MeOThr]$^2$-[(D)MeAla]$^3$-[MeVal]$^5$-Ciclosporin | >10 | 0.45 |
| j) [8'-hydroxy-MeBmt]$^1$-Ciclosporin | 10.6 | 0.56 |
| k) [MeAla]$^6$-Ciclosporin | 5.2 | 1.34 |
| l) [γ-hydroxy-MeLeu]$^9$-Ciclosporin | >10 | 0.31 |
| Ciclosporin | 8.45 | 0.53 |

The Active Compounds are indicated both for the prevention of AIDS in asymptomatic HIV-positive patients and in the treatment of patients suffering from AIDS. In the patients in which AIDS has appeared the administration of the Active Compounds reverse the T4-cell depletion associated with AIDS, induce regression of AIDS-related disorders, such as Kaposi's sarcoma, and reduce the liklihood of new opportunistic infections.

Thus the invention provides a process for the treatment and the prevention of the acquired immunodeficiency syndrome and other disorders induced by the HIV-1 virus in a patient infected with said virus, comprising administering to said patient an effective amount of an Active Compound of the invention.

The Active Compound may be administered by any conventional route, in particular enterally, e.g. orally, for example in the form of solutions for drinking, tablets or capsules or parenterally, for example in the form of injectible solutions or suspensions. By the intravenous route an indicated daily dosage may be from 1 to 20 mg/kg, preferably from 3 to 10 mg/kg, and by the oral route from 1 to 50 mg/kg, preferably from 7 to 20 mg/kg.

The toxicity of the Active Compounds is believed to be similar to that of Ciclosporin. As the Active Compounds are not immunosuppressive, certain side effects of Ciclosporin related to immunosuppression are avoided. Other side effects associated with Ciclosporin, however, particularly nephrotoxicity in long term use, may also be associated with the Active Compounds.

Preferred galenic formulations for the Active Compounds include those based on microemulsions as described in British Patent Application 2 222 770A, which include topical as well as oral forms; also oral and injectable forms obtained from solid solutions comprising a fatty acid saccharide monoester, e.g. saccharose monolaurate, as described in British Patent Application 2 209 671A. Suitable unit dosage forms for oral administration comprise e.g. from 25 to 200 mg Active Compound per dosage.

| Formulation Example A: | |
|---|---|
| Product of Ex. 1 | 50.0 mg |
| Glycofurol 75 | 180.0 mg |
| Miglyol 812 | 90.0 mg |
| Cremophor RH40 | 180.0 mg |
| alpha-Tocopherol | 0.5 mg |
| Formulation Example B: | |
| Product of Ex. 1 | 100.0 mg |

| | |
|---|---|
| Tetraglycol | 20.0 mg |
| Captex 800 | 20.0 mg |
| Nikkol HCO-40 | 860.0 mg |
| Butylhydroxytoluene(BHT) | 1.0 mg |
| Formulation Example C: | |
| Product of Ex. 1 | 25.0 mg |
| Glycofurol 75 | 100.0 mg |
| Miglyol 812 | 35.0 mg |
| Cremophor RH 40 | 90.0 mg |
| Butylhydroxyanisole(BHA) | 0.2 mg |
| Formulation Example D: | |
| Product of Ex. 1 | 10.0 mg |
| Tetraglycol | 10.0 mg |
| Myritol | 5.0 mg |
| Cremophor RH 40 | 75.0 mg |
| alpha-Tocopherol | 0.1 mg |

The individual components of these formulations, as well as the methods for their preparation, are fully described in British Patent Application 2 222 770, the contents of which are incorporated herein by reference.

We claim:

1. A non-immunosuppressive, cyclophilin-binding compound of Formula II

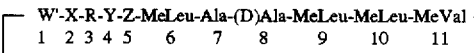

where

W' is MeBmt or dihydro-MeBmt;

X is αAbu, Val, Thr, Nva or MeOThr;

R is Sar or (D)-MeAla;

Y is MeLeu, γ-hydroxy-MeLeu, MeIle, MeVal, MeThr, MeAla, MeaIle or MeaThr; and

Z is Val, Leu, MeVal or MeLeu;

provided that 1) when Y is MeLeu or MeAla then Z is MeVal or MeLeu; and 2) when W' is MeBmt, R is Sar, and Y is γ-hydroxy-MeLeu, then Z is other than Val.

2. A compound according to claim 1 of Formula II

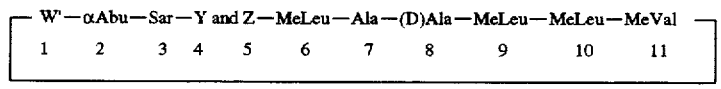

in which

W' is MeBmt or dihydro-MeBmt;

Y is γ-hydroxy-MeLeu, MeVal, MeThr, or MeIle; and

Z is Val or MeVal;

provided that when W' is MeBmt, Y' is other than γ-hydroxy-MeLeu.

3. A non-immunosuppressive, cyclophilin-binding compound selected from the group consisting of:

[dihydro-MeBmt]$^1$-[γ-hydroxy-MeLeu]$^4$-Ciclosporin,

[MeVal]$^4$-Ciclosporin,

[MeIle]$^4$ -Ciclosporin,

[MeThr]$^4$-Ciclosporin,

[Nva]$^2$-[γ-hydroxy-MeLeu]$^4$-Ciclosporin,

[γ-hydroxy-MeLeu]$^4$-[γ-hydroxy-MeLeu]$^6$ -Ciclosporin,

[MeVal]$^5$-Ciclosporin, and

[MeOThr]$^2$-[(D)MeAla]$^3$-[MeVal]$^5$-Ciclosporin.

4. A pharmaceutical composition comprising a compound as described in claims 1, 2 or 3 together with a pharmaceutically acceptable carrier or diluent, therefor.

5. The compound of claim 3 which is [MeIle]$^4$-ciclosporin.

6. The pharmaceutical composition according to claim 4 comprising [MeIle]$^4$-ciclosporin and a pharmaceutically acceptable carrier therefor.

* * * * *